US008873806B2

(12) United States Patent
Kiest, Jr.

(10) Patent No.: US 8,873,806 B2
(45) Date of Patent: Oct. 28, 2014

(54) METHOD AND MEANS FOR DETERMINING CHANGE IN PIPE DIAMETER

(71) Applicant: LMK Technologies, LLC, Ottawa, IL (US)

(72) Inventor: Larry W. Kiest, Jr., Ottawa, IL (US)

(73) Assignee: LMK Technologies, LLC, Ottawa, IL (US)

( * ) Notice: Subject to any disclaimer, the term of this patent is extended or adjusted under 35 U.S.C. 154(b) by 203 days.

(21) Appl. No.: 13/644,546

(22) Filed: Oct. 4, 2012

(65) Prior Publication Data
US 2014/0098384 A1 Apr. 10, 2014

(51) Int. Cl.
G06K 9/00 (2006.01)
(52) U.S. Cl.
USPC .................... 382/103; 700/97; 348/135
(58) Field of Classification Search
USPC ......... 382/100, 103, 106, 108, 141, 165, 181, 382/190, 195, 199, 206; 700/90, 95, 97, 98, 700/109; 348/92, 135
See application file for complete search history.

(56) References Cited

U.S. PATENT DOCUMENTS

| 4,406,584 | A  | * | 9/1983  | Stepp ........................... 416/41 |
| 4,584,676 | A  | * | 4/1986  | Newman ...................... 367/108 |
| 6,683,641 | B1 | * | 1/2004  | MacCracken et al. ........... 348/82 |
| 7,693,322 | B2 | * | 4/2010  | Carroll et al. ................. 382/141 |
| 8,327,556 | B2 | * | 12/2012 | Das et al. ...................... 33/543.1 |
| 2005/0120812 | A1 | * | 6/2005 | Edwin et al. ................. 73/865.8 |
| 2009/0320542 | A1 | * | 12/2009 | Kephart ........................... 72/49 |

* cited by examiner

Primary Examiner — Anand Bhatnagar
(74) Attorney, Agent, or Firm — McKee, Voorhees & Sease

(57) ABSTRACT

A diameter sensing assembly is provided for determining the location of a change in diameter in a pipe from a remote location outside of the pipe. The assembly includes an imaging device operatively connected to an imaging cable and a diameter sensing device operatively connected to a sensing cable. The sensing device is positioned generally forward of the imaging device, and includes a plurality of flexible arms that are rigid enough to stay horizontal, but flexible enough to bend or depress easily. The two cables are connected to one another such that the entire assembly is able to be moved through a pipe at a constant speed. Marks are placed on one of the cables to determine the length to the change in diameter, and the length of portions of pipes having different diameters.

35 Claims, 7 Drawing Sheets

METHOD AND MEANS FOR DETERMINING CHANGE IN PIPE DIAMETER

FIELD OF THE INVENTION

The present invention relates generally to sewer liner repair. More particularly, but not exclusively, the invention relates to a method and means for determining the location of a change in the diameter of a sewer pipe from a remote location prior to repairing the pipe.

BACKGROUND OF THE INVENTION

Cured-in-place pipe repair (CIPP) has been used to repair damaged main sewer pipes or lateral sewer pipes as well as other types of conduits. Generally, a liner tube is impregnated with a resinous material, and is positioned in a pipe adjacent a damaged area of pipe. The liner tube is pressed against the wall of the damaged area of the pipe and the resin is allowed to cure, thus leaving a renewed pipe wall. In addition, the liner tube is either pulled in place or inflated and inverted into the pipe to the damaged area in need of repair.

Liner tubes are generally formed from a flat piece of material, which is sized to be the correct length and width to fully cover the lateral pipe wall. The material is then rolled together, with the two ends of the width of the liner connected by stitching or welding, to form the tube. The diameter of the liner tube must be the same as the diameter of the lateral pipe. If the liner tube has a diameter less than the diameter of the lateral pipe, ripping or tearing of the liner could occur. If, on the other hand, the liner tube has a diameter greater than the diameter of the lateral pipe, the liner tube may fold over itself, or create bulges in the cured liner. These folds or bulges could cause blockages in the lateral pipe, and would need to be cut or sanded out. The extra work would be time consuming and expensive.

At times, lateral pipes have varying diameters along their lengths. The variable diameter pipes require custom liners to be constructed. A first length of tubular liner will be formed to repair a length of the pipe having a certain diameter, and a second length of liner will have to be formed to line up with the section of the pipe having the second diameter. To repair the pipes, either the liners will be positioned and cured separately, or at the same time. A problem exists in either method, however. It is important to have the right diameter of liner tube for the appropriate section of pipe, with the change in diameter of the liner tube corresponding to the exact location of the change in diameter of the pipe. If this is not the case, the above-mentioned problems of tearing or folding will occur.

As lateral pipes may be lengthy, it has been difficult to accurately determine both the location of the change in diameter of pipe, as well as the value of the change. Therefore, there is a need in the art for a method and means of determining the location of and amount of change in a lateral pipe diameter. There is also a need to determine the information as quickly as possible to be able to efficiently repair the wall of the pipe.

SUMMARY OF THE INVENTION

It is therefore a primary object, feature, and/or advantage of the present invention to provide an improved method and means of determining the location and value of a change in the diameter of a lateral pipe that improves or solves deficiencies in the art.

It is another object, feature, and/or advantage of the present invention to provide a method and means of determining a change in diameter of a lateral pipe that can be determined from a remote location outside of the lateral pipe.

It is another object, feature, and/or advantage of the present invention to provide a method and means of determining a change in diameter of a lateral pipe to construct a liner assembly to repair a section of wall of the lateral pipe.

It is another object, feature, and/or advantage of the present invention to provide a method and means of determining a change in diameter of a lateral pipe using a device positioned forward of an imaging device.

It is another object, feature, and/or advantage of the present invention to provide a method and means of determining a change in diameter of a lateral pipe via access through a cleanout pipe.

It is another object, feature, and/or advantage of the present invention to provide a method and means of repairing a damaged section of a wall of a lateral pipe.

It is another object, feature, and/or advantage of the present invention to provide a method of means of determining a change in the diameter of a lateral pipe using a device having a predetermined diameter.

It is another object, feature, and/or advantage of the present invention to provide a method and means of determining a change in the diameter of a lateral pipe using spring steel the bends when the pipe diameter is less than a predetermined diameter.

These and/or other objects, features, and advantages of the present invention will be apparent to those skilled in the art. The present invention is not to be limited to or by these objects, features and advantages, and no single embodiment need exhibit every object, feature, and/or advantage.

According to one aspect of the present invention, a method of determining the location of a change in diameter of a pipe is provided. The method includes providing a diameter sensing assembly including an imaging device and a sensing device operatively connected to the imaging device and positioned at least partially forward of the imaging device, the sensing device comprising a plurality of flexible arms extending radially outwardly. The sensing assembly is inserted into the pipe. The assembly is then moved through the length of the pipe, and imaging data is acquired of the plurality of arms of the sensing device in relation to a wall of the pipe as the assembly moves through the pipe. The imaging data is used to determine the location of a change in diameter of the pipe.

According to another aspect of the present invention, a sensing assembly for determining the location of a change in diameter of a lateral pipe along the length of the lateral pipe used in connection with a sewer system from a remote location is provided. The sensing assembly includes an imaging device, an imaging cable, and a sensing device. The imaging device is used for acquiring imaging data inside the lateral pipe. The imaging cable is operatively connected to the imaging device and configured to transmit imaging data to the remote location. The sensing device is operatively connected to the imaging device and at least partially forward of the imaging device, the sensing device comprising a plurality of flexible arms extending radially outwardly. The diameter of the sensing device is equal to or slightly less than a predetermined diameter of the lateral pipe.

According to yet another aspect of the present invention, a method of repairing a section of a wall of a lateral pipe is provided. The method includes determining the location of a change in diameter of the lateral pipe by providing a diameter sensing assembly comprising an imaging device and a sensing device positioned at least partially forward of the imaging device, the sensing device comprising a plurality of flexible arms extending radially outwardly, and acquiring imaging data of the sensing device in relation to the wall of the lateral pipe as the assembly moves through the pipe. A liner assembly is assembled based on the number and location of changes in diameter along the length of the section of lateral pipe, the liner assembly comprising a bladder tube and a liner tube impregnated with a resinous material capable of curing and hardening. The liner assembly is inserted into the lateral pipe, wherein the diameter of the liner assembly matches the diameter of the lateral pipe along the length of the section of lateral pipe being repaired. The liner tube is then pressed against a wall of the lateral pipe, and the resinous material is allowed to cure and harden. A bladder tube may be used to press the liner tube against the lateral pipe and may be removed following cure of the resinous material capable of curing and hardening, leaving the liner tube cured in place along a section of the wall of the lateral pipe.

DETAILED DESCRIPTION OF THE PREFERRED EMBODIMENTS

Figure 1:
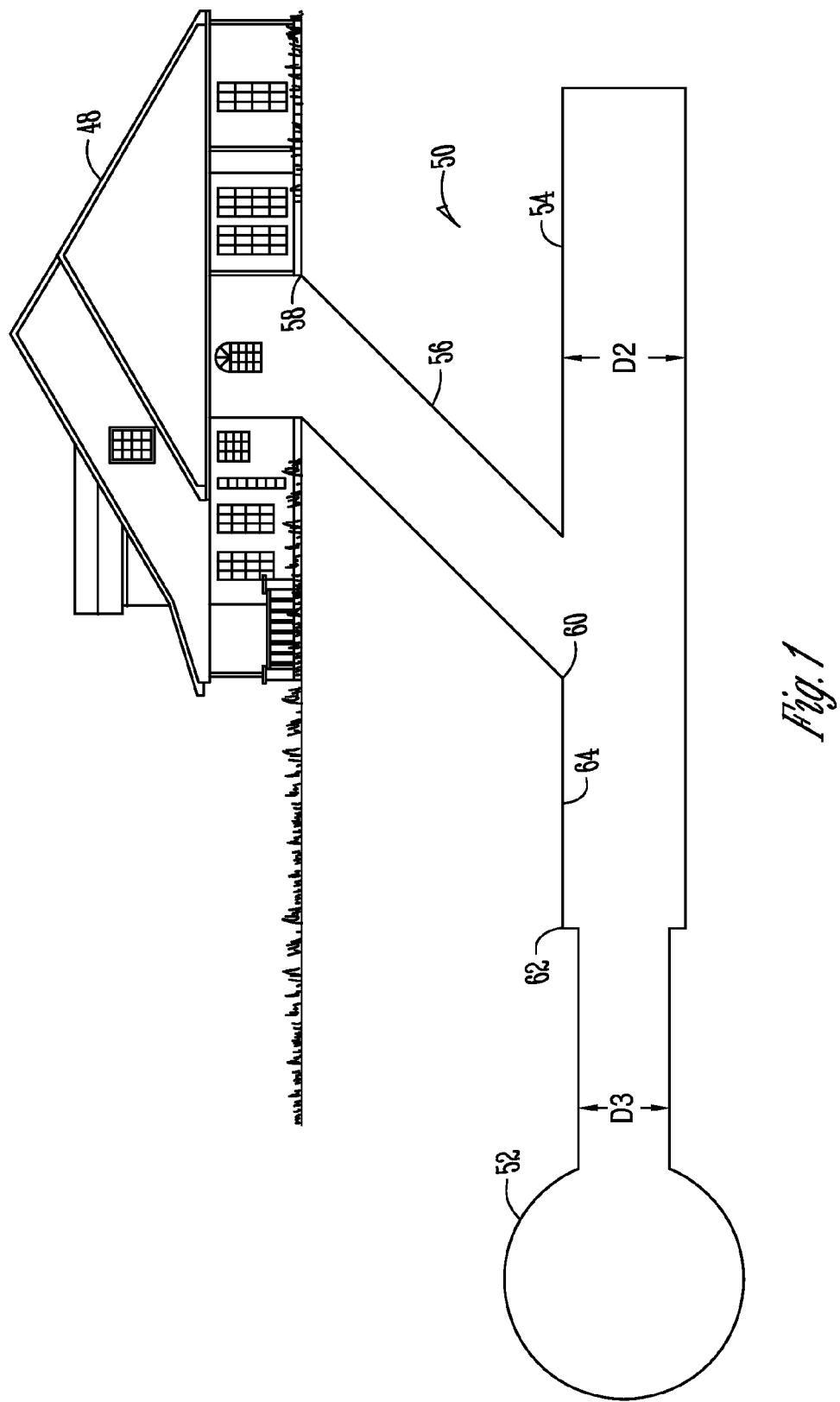
FIG. 1 is an exemplary view of a sewer pipe system including a house, cleanout pipe, lateral pipe having a change in diameter, and a main pipe.

FIG. 1 is a sectional view of a sewer pipe system 50 including a house 48, main pipe 52, a lateral pipe 54, and a cleanout pipe 56. The cleanout pipe 56 extends from the house 48 and includes an opening 58. The cleanout pipe ends at an opening 60 of the lateral pipe 54. In FIG. 1, the cleanout pipe is shown to extend from the lateral pipe in a wye shape. However, it should be appreciated that the cleanout pipe may also extend from the lateral pipe at an approximately 90° angle, forming a tee shape. The present invention is not to be limited to one of the shapes and can be used with either pipe orientation. The lateral pipe is tubular-shaped and includes an inner wall 64, which may form cracks or other defects. In addition, due to the age and requirements of the lateral pipe 54, the pipe may contain varying diameters D2, D3. The lateral pipe may be a certain diameter D2 for a length, and then at a position 62, the diameter may change. As shown in FIG. 1, the diameter 12 of the lateral pipe is reduced after the change in diameter 62 to a lesser diameter D3 before terminating at the main pipe 52. It should also be noted that the lateral pipe may extend from the main pipe in either a wye or tee shape, as discussed above in regards to the cleanout pipe.

Figure 2:
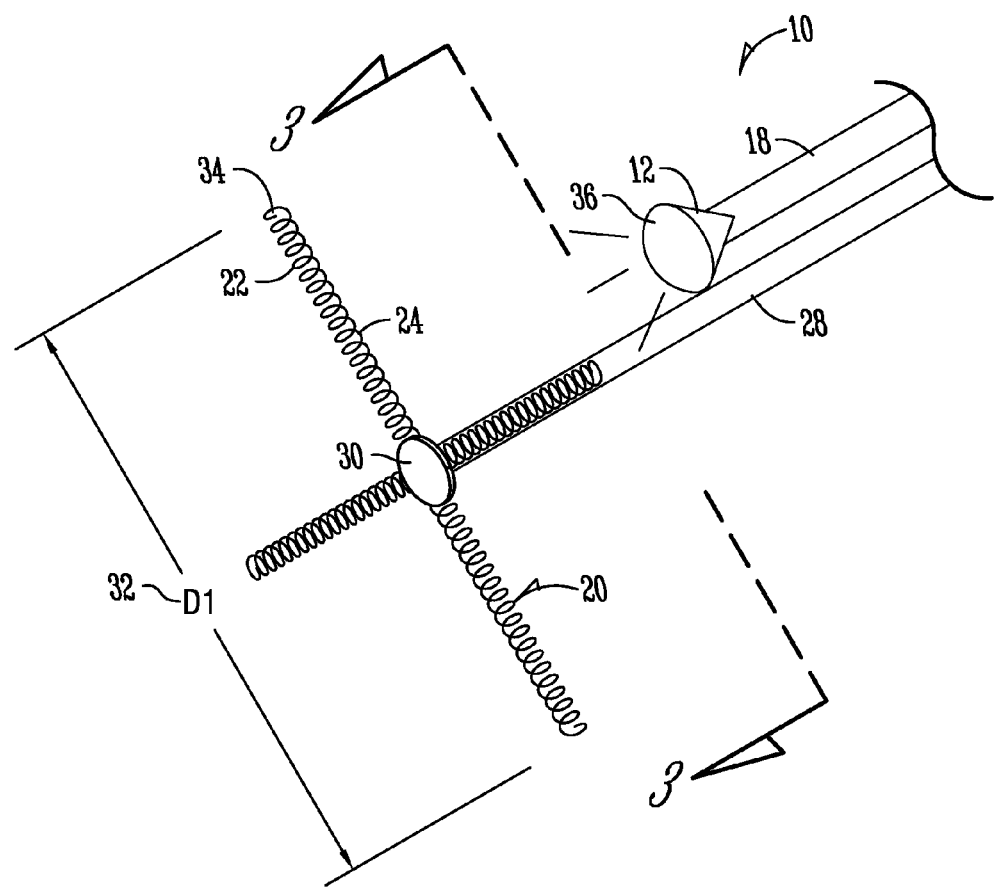
FIG. 2 is a perspective view of the diameter sensing assembly of the present invention.

FIG. 2 is a perspective view of a diameter sensing assembly 10 used to determine the position of a change in diameter along the length of a pipe. The diameter sensing assembly 10 includes an imaging device 12, an imaging cable 18, a sensing device 20, and a sensing device cable 28. The imaging device 12 may be any device capable of obtaining and relaying imaging data 14 from the inside of a pipe to an imaging viewer 16 at a remote location 66 outside of the pipe. Therefore, the imaging device 12 may be a camera, a sensor, or the like. FIG. 2 shows the imaging device 12 to be a camera including a lens for viewing the area forward of the camera. The imaging cable 18 comprises a conductive material capable of transferring imaging data from the imaging device to the imaging viewer. However, it should be appreciated that the imaging device 12 may also relay imaging data 14 wirelessly. In such case, the imaging cable is used to support the imaging device and to aid in moving the sensing assembly. Therefore, the imaging cable is a generally rigid cable.

Operatively connected to the imaging device and/or imaging cable is a sensing device 20. The sensing device 20 includes a plurality of flexible arms 22 radially extending radially outwardly from a central axis 30. The central axis may be a coupling for attaching the arms thereto. Preferably, the arms 22 are comprised of a spring steel 24 material, but any semi-rigid material that is capable of holding horizontally, while being easily depressible would suffice. FIG. 2 shows the arms formed of spring steel in a spiral manner, much like a slinky. The steel is strong enough for the arms to hold themselves outwardly, but flexible enough that they are easily bent or depressed. The arms 22 and central axis or coupling 30 are connected to a sensing device cable 28, which comprises a material rigid enough to push or move the sensing device 20 through a pipe. It should also be noted that the sensing device is forwardly connected to the imaging device 12 such that the imaging data obtained by the imaging device includes the sensing device. It should also be noted that the arms 22 are sized such that the ends 34 of the arms equal a predetermined diameter 32, which is a diameter D1 sized equal to a known diameter the interior of a pipe.

Figure 3:
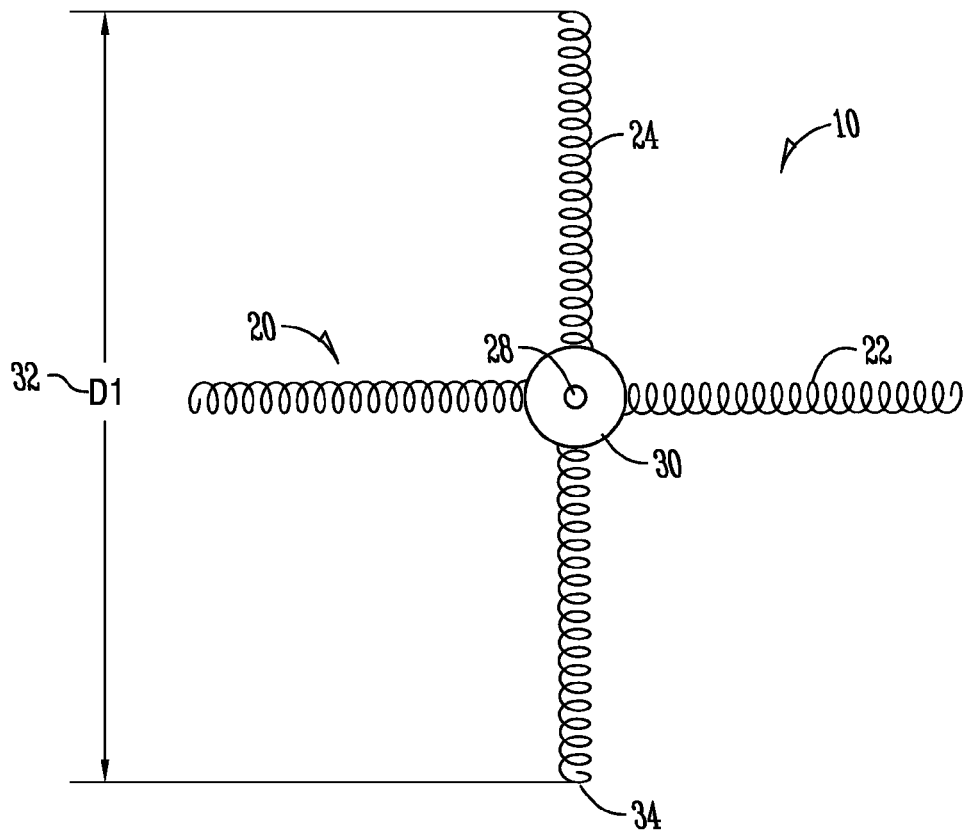
FIG. 3 is a cross-sectional view of the diameter sensing assembly according to line 3-3 of FIG. 2.

FIG. 3 is a cross-sectional view of the diameter sensing assembly 20 according to line 3-3 of FIG. 2. FIG. 3 shows that the arms 22 are evenly spaced about the central axis or coupling 30. It should also be noted that the arms 22 are of equal length such that the length from one end 34 to another is equal to a predetermined diameter or length 32. This diameter D1 is equal to a known diameter of a pipe containing varying diameters through the length of the pipe.

Figure 4:
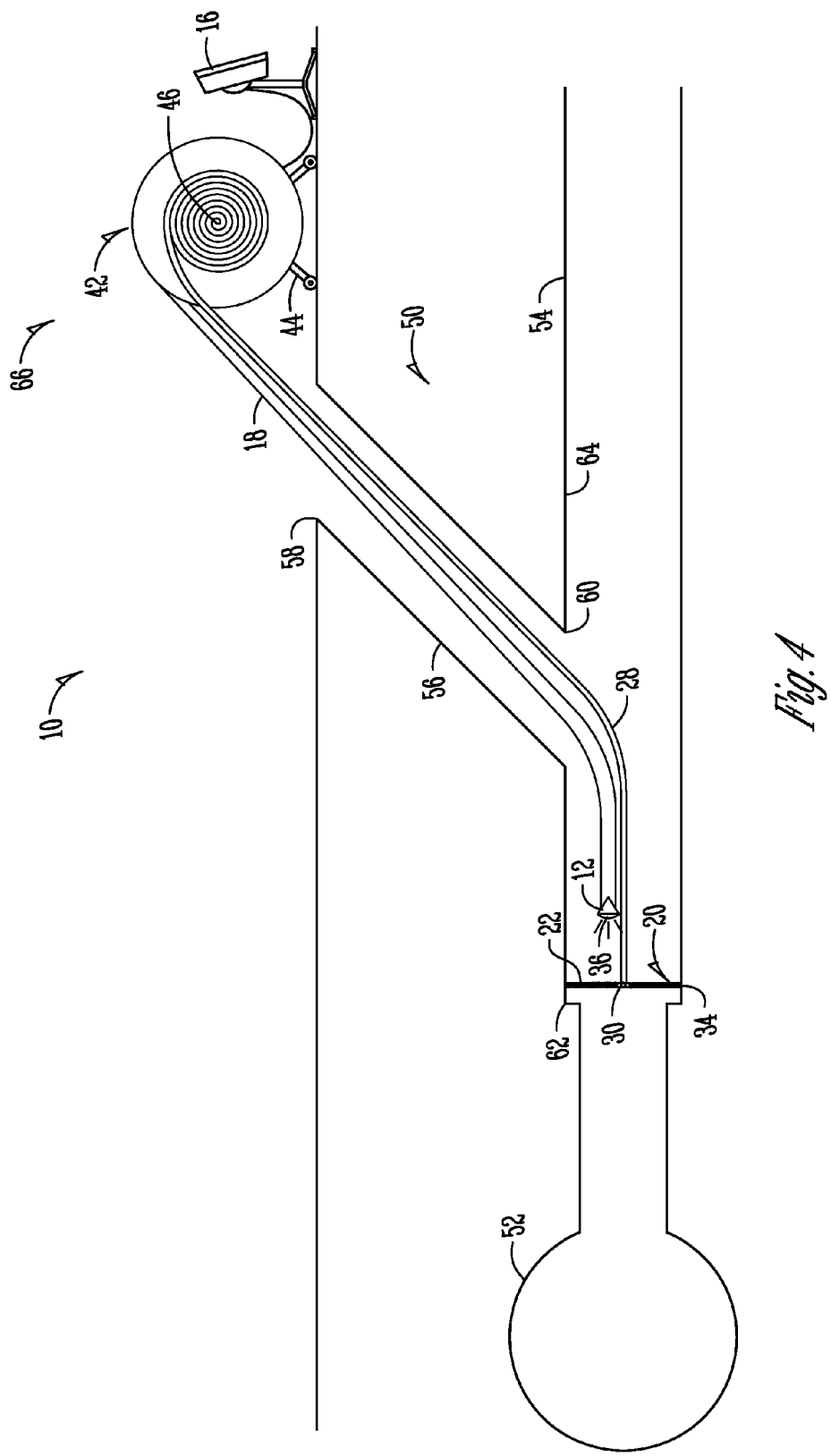
FIG. 4 is a sectional view of the sewer pipe system showing the diameter sensing assembly positioned within the lateral pipe.

FIG. 4 is a sectional view of the sewer pipe system 50 showing the diameter sensing assembly 10 positioned within a lateral pipe 54 at a position of known diameter D2. The imaging cable 18 and the sensing device cable 28 are connected to one another such that the assembly 10 moves through the pipe system at a constant speed. The two cables may be connected to a reel 42 positioned at a remote location 66 outside of the pipes. The reel 42 includes reel supports 44 and a center roller 46. In addition, an imaging viewer 16 is operatively attached to the cables via the reel such that the viewer displays imaging data obtained by the imaging device 12. The imaging viewer 16 is a device, such as a monitor, for viewing imaging data relayed from the imaging device.

In use, the diameter of a lateral pipe 54 is determined. This may be done using the apparatus and method of U.S. patent application Ser. No. 13/628,443, which is hereby incorporated by reference in its entirety. A sensing device 22, having a diameter equal to the predetermined diameter of the lateral pipe is attached to the sensing device cable 18. Common lateral pipe diameters are four, five, or six inches. Therefore, having premanufactured sensing devices of these three diameters at the remote location is beneficial. This assembly is attached to an imaging device 12 and imaging cable 18 to form the diameter sensing assembly 10.

The diameter sensing assembly is then inserted through the opening 58 of the cleanout pipe 56 and further inserted through the opening 60 of the lateral pipe 54 to the position of known lateral pipe diameter. Imaging data is viewed at the imaging viewer 16 while the assembly 10 is moved through the pipe system 50.

Figure 5:
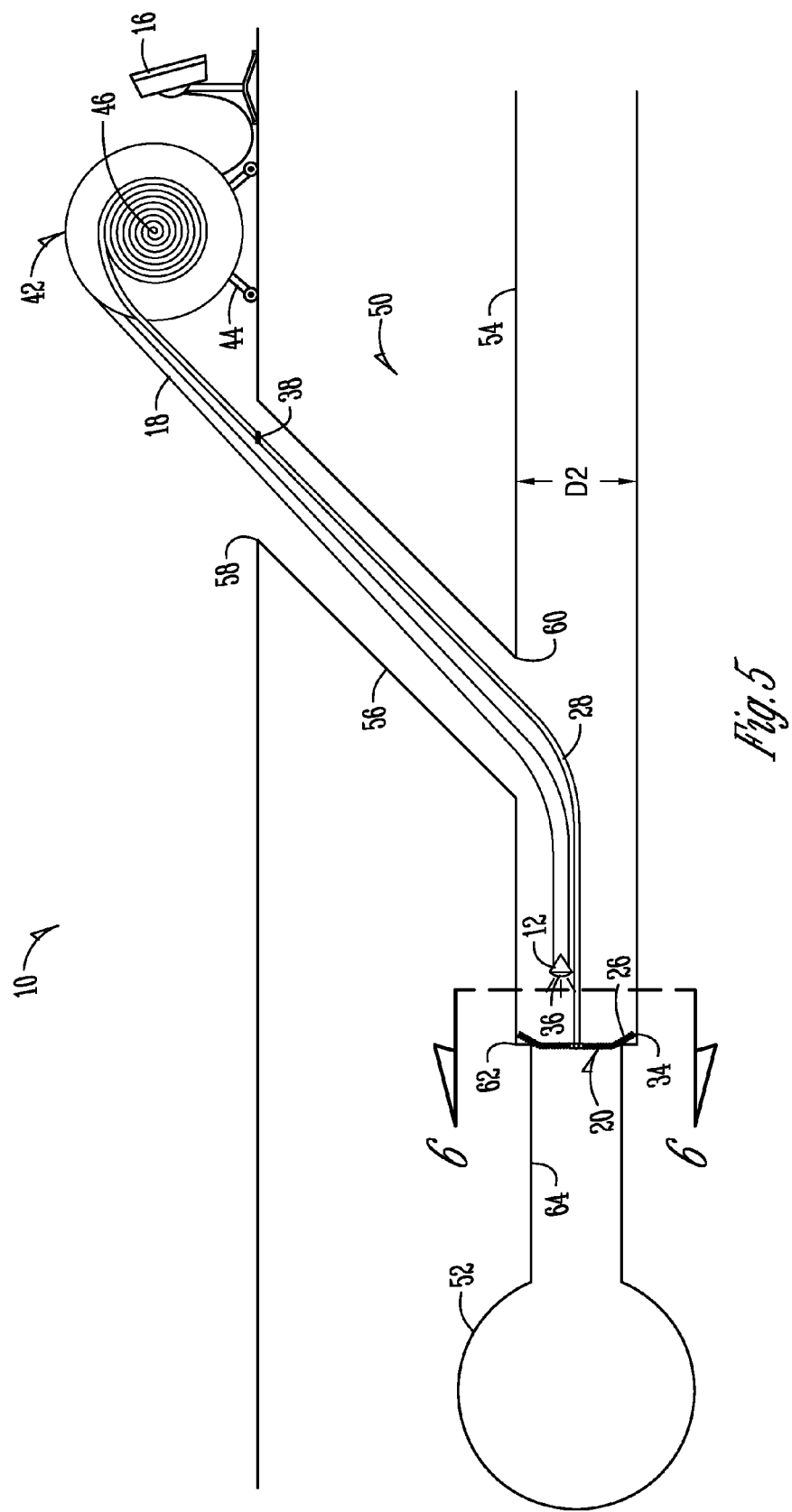
FIG. 5 is a sectional view similar to FIG. 4 showing the assembly at the location of the change in diameter in the lateral pipe.

The assembly 10 is continually moved through the lateral pipe 54 to a position 62 where the diameter of the lateral pipe changes. As shown in FIG. 5, the diameter of the lateral pipe 54 is reduced at the position 62. When the assembly 10 continues through the portion of the lateral pipe having a smaller diameter, the flexible arms 22 will be bent or depressed rearwardly towards the imaging device 12. The imaging device 12 will be obtaining imaging data 14, including images of the arms 22. When the imaging data shows that the arms begin to bend or depress, the assembly has signified the position 62 of a change in diameter of the lateral pipe. A mark 38 is placed on the sensing device cable 28 to designate the distance from the opening 58 of the cleanout pipe 56 to the location 62 of the change in diameter of the lateral pipe. An additional mark (not shown) may be placed on the cable when the arms 22 of the assembly 10 pass through the opening 60 of the lateral pipe. Therefore, the distance (shown as d2 in FIG. 7) between the two marks would represent the length of lateral pipe of the known and predetermined diameter 32.

Figure 6:
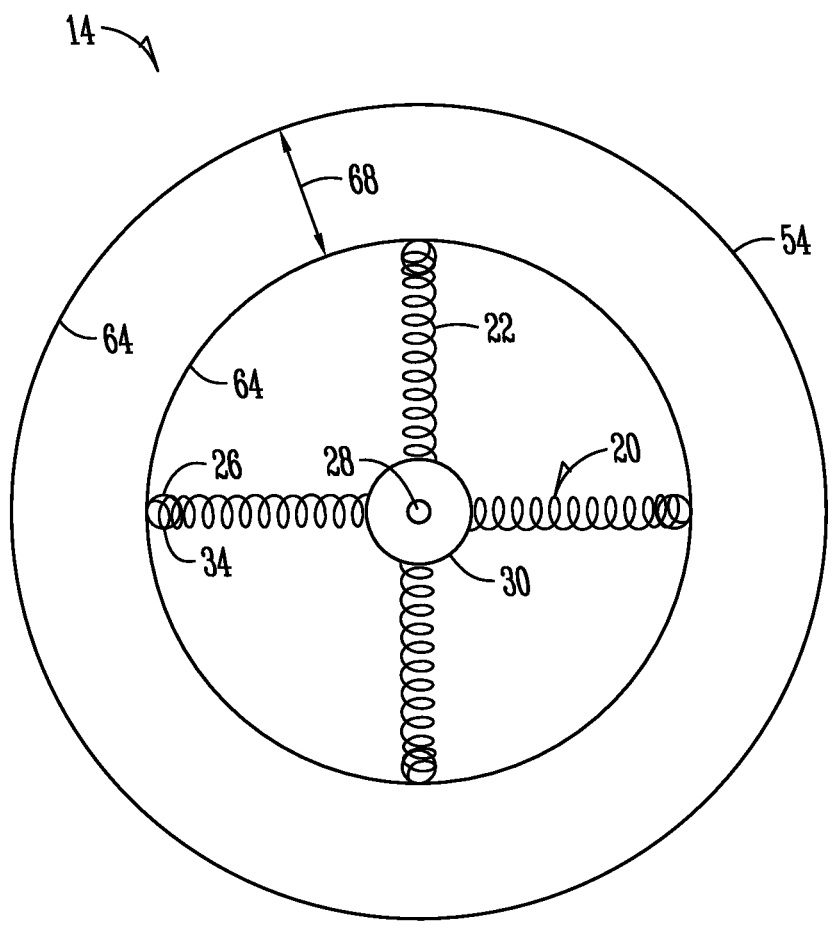
FIG. 6 is a cross-sectional view of the assembly according to line 6-6 of FIG. 5 showing imaging data within the pipe.

FIG. 6 is a cross-sectional view of the assembly 10 according to line 6-6 of FIG. 5 showing imaging data 14 within the lateral pipe 54. FIG. 6 is an example of what might be shown on the imaging viewer 16, in the instance that the imaging device 12 is a camera. The image is of the diameter sensing assembly 10 in the lateral pipe at the location 62 of the change in diameter. Therefore, the imaging device 12 obtains images of the wall 64 of the lateral pipe at the predetermined or larger diameter, the wall 64 of the smaller diameter portion of lateral pipe, and the bent arms 26 of the sensing device 20. This gives the difference in diameter 68 between the larger portion and smaller portion of the lateral pipe. Because the length of the arms is greater than the diameter of the smaller diameter portion of the lateral pipe, the arms will bend or be depressed rearwardly. Therefore, the imaging data would show the circular ends 34 of the plurality of arms 22 facing the imaging device 12. However, it should be noted that if the arms are not spiral or circular, any change in the arms may designate a smaller diameter.

Figure 7:
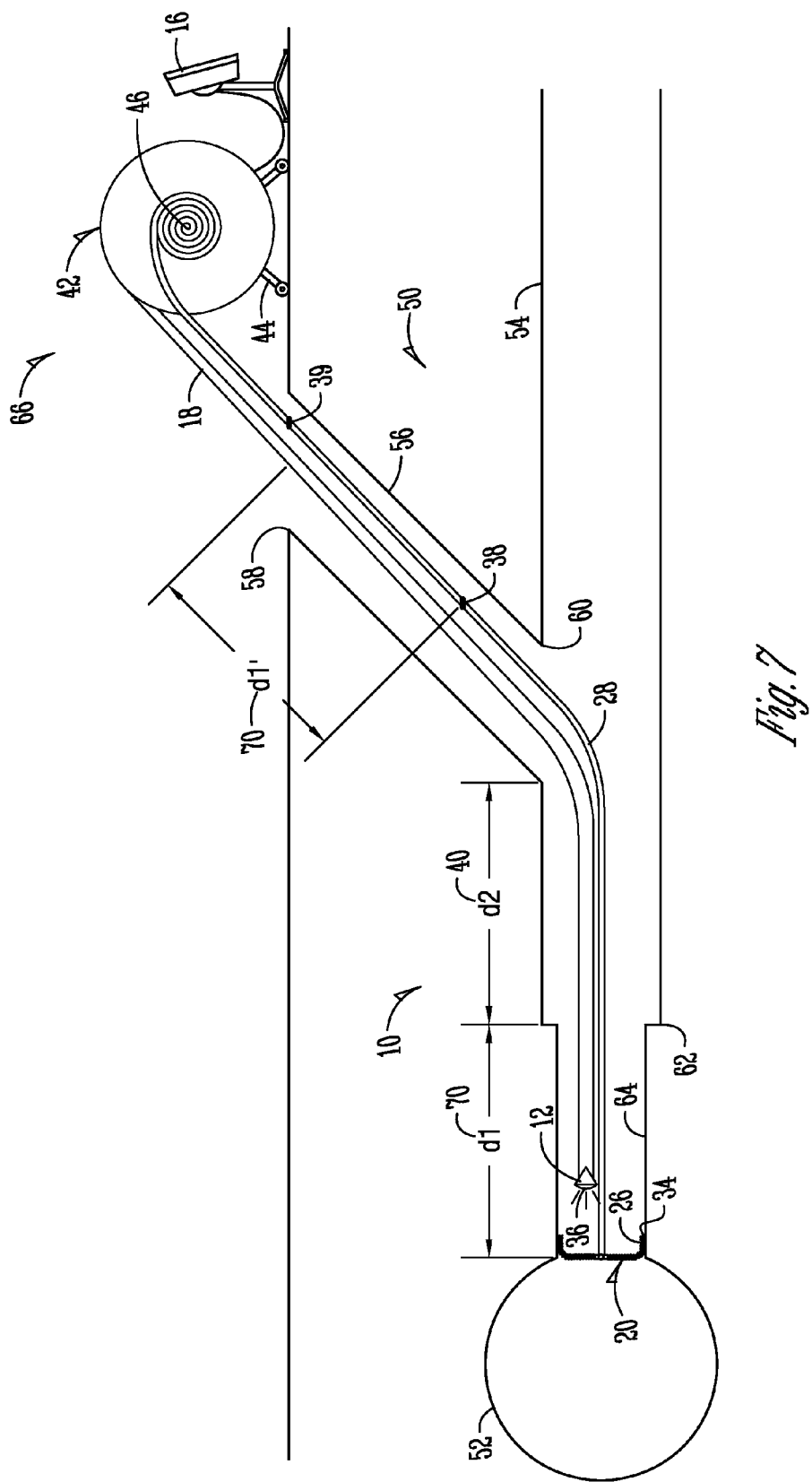
FIG. 7 is a sectional view of the assembly at a second or end position within the lateral pipe.

FIG. 7 shows where the diameter sensing assembly 10 is moved further through the smaller diameter portion (d1) of the lateral pipe 54 until the arms reach the end of the lateral pipe, which is where the lateral pipe meets a main pipe 52. At this position, an additional mark 39 is placed on the sensing device cable 28. The distance (d1 and d1') between the two marks designate the length 70 of lateral pipe having the smaller diameter.

The location and length of the change in lateral pipe diameter is needed for repairing the lateral pipe from defects in the wall 64 of the pipe. The wall is repaired by cured-in-place pipe (CIPP) lining. For example, methods and apparatuses of repairing a lateral pipe with a bladder tube and liner tube are disclosed in U.S. Pat. Nos. 5,765,597; 6,695,013; and 7,343,937, which are hereby incorporated by reference in their entireties. However, the liner tube used to line the wall of the lateral pipe must be custom made in instances where the diameter of the pipe varies. In the pipe shown in FIG. 7, a portion of liner tube having a diameter D2 of predetermined diameter will be connected to a second portion having a diameter D3 of a lesser amount. The length of the first portion is equal to the length d2 determined above, and the length of the second portion is also equal to the length d1/d1' determined above. Therefore, the correct diameter portion of liner tube will be used to repair the wall of the lateral pipe. The correct diameter of liner tube is required such that the cured liner, which has been previously saturated with a resinous material, will not include any tears, rips, or folds, which would require additional repair. The two portions of liner tube may be connected by sewing, fusing, or gluing the portions together, depending on whether the tube includes a coating.

The invention has been shown and described above with reference to the preferred embodiments, and it is understood that many modifications, substitutions, and additions may be made all within the intended spirit and scope of the invention.

What is claimed is:

1. A method of determining the location of a change in diameter of a pipe, comprising:
   providing a diameter sensing assembly including an imaging device and a sensing device operatively connected to the imaging device and positioned at least partially forward of the imaging device, the sensing device comprising a plurality of flexible arms extending radially outwardly;
   inserting the diameter sensing assembly into the pipe;
   moving the diameter sensing assembly through the length of the pipe;
   acquiring imaging data of the plurality of arms of the sensing device in relation to a wall of the pipe as the assembly moves through the pipe; and
   using the imaging data to determine the location of a change in diameter of the pipe.

2. The method of claim 1 wherein the flexible arms comprise spring steel.

3. The method of claim 1 further comprising determining the diameter of the pipe at a location to size the flexible arms to a predetermined diameter.

4. The method of claim 3 wherein the flexible arms are sized to be in contact with the wall of the pipe for the predetermined diameter of the pipe.

5. The method of claim 4 wherein the plurality of flexible arms are the same length.

6. The method of claim 1 wherein the imaging device is a camera.

7. The method of claim 6 wherein the imaging data is a picture of the plurality of flexible arms moving through the pipe.

8. The method of claim 1 further comprising viewing the imaging data at a remote location.

9. The method of claim 8 wherein the imaging data is viewed at an imaging viewer.

10. The method of claim 1 wherein a change in diameter of the pipe occurs when the plurality of flexible arms bend.

11. The method of claim 1 wherein the sensing assembly further comprises an imaging cable operatively connected to the imaging device and used to move the sensing assembly through the pipe.

12. The method of claim 11 further comprising marking the imaging cable at an opening of the pipe when a change in diameter of the pipe is determined.

13. The method of claim 12 wherein the marking is used to measure the distance from the imaging device to the marking that is equal to the distance between the opening of the pipe and the location of the change in diameter in the pipe.

14. The method of claim 1 further comprising inserting the sensing assembly through a cleanout pipe before the assembly is inserted into the pipe.

15. The method of claim 1 wherein the flexible arms are radially mounted about a same central axis.

16. A sensing assembly for determining the location of a change in diameter of a lateral pipe along the length of the lateral pipe used in connection with a sewer system from a remote location, comprising:
   an imaging device for acquiring imaging data inside the lateral pipe;
   an imaging cable operatively connected to the imaging device and configured to transport imaging data to the remote location;
   a sensing device operatively connected to the imaging device and at least partially forward of the imaging device, the sensing device comprising a plurality of flexible arms extending radially outwardly;
   wherein the diameter of the sensing device is equal to a predetermined diameter at a beginning of the lateral pipe and the imaging device acquires imaging data of the sensing device in and along the lateral pipe.

17. The assembly of claim 16 wherein the plurality of flexible arms comprise steel spring.

18. The assembly of claim 17 wherein the plurality of flexible arms is spring shaped to allow the arms to bend.

19. The assembly of claim 18 wherein a bend in the plurality of springs signals a change in the diameter of the lateral pipe.

20. The assembly of claim 16 further comprising an imaging viewer to view the imaging data acquired by the imaging device.

21. The assembly of claim 20 wherein the imaging viewer is a screen.

22. The assembly of claim 16 wherein the imaging device is a camera.

23. The assembly of claim 22 wherein the imaging data is a picture.

24. The assembly of claim 22 wherein the imaging data is a video.

25. The assembly of claim 16 wherein the imaging cable is further adapted to move the assembly through the lateral pipe.

26. The assembly of claim 16 wherein the imaging data comprises images of the plurality of flexible arms in relation to the wall of the lateral pipe as the assembly moves through the lateral pipe.

27. The assembly of claim 16 wherein the flexible arms are radially mounted on a same centralized axis.

28. A method of repairing a section of a wall of a lateral pipe, comprising:
   determining the location of a change in diameter of the lateral pipe by providing a diameter sensing assembly comprising an imaging device and a sensing device positioned at least partially forward of the imaging device, the sensing device comprising a plurality of flexible arms extending radially outwardly, and acquiring imaging data of the sensing device in relation to the wall of the lateral pipe as the assembly moves through the pipe;
   assembling a liner assembly, comprising a bladder tube and a liner tube impregnated with a resinous material capable of curing and hardening, based on the number and location of changes in diameter along the length of the section of lateral pipe;
   inserting the liner assembly into the lateral pipe, wherein the diameter of the liner assembly matches the diameter of the lateral pipe along the length of the section of lateral pipe being repaired;
   pressing the liner tube against a wall of the lateral pipe;
   allowing the resinous material to cure and harden; and
   removing the bladder tube from the lateral pipe to leave the liner tube cured in place in the lateral tube along a length of the section of the wall of the lateral pipe.

29. The method of claim 28 wherein the liner assembly is inverted into the lateral pipe.

30. The method of claim 29 further comprising inflating the bladder tube within the lateral pipe.

31. The method of claim 28 wherein the liner assembly changes diameter at the same location that the lateral pipe changes diameter.

32. The method of claim 28 wherein the step of determining the location of a change in diameter of the lateral pipe further comprises inserting the diameter sensing assembly and moving the assembly through the lateral pipe.

33. The method of claim 28 wherein the sensing device is of a predetermined diameter.

34. The method of claim 28 wherein the step of determining the location of a change in diameter of the lateral pipe further comprises using the imaging data to determine the location of a change in diameter of the lateral pipe.

35. The method of claim 34 further comprising marking the diameter sensing assembly at the location of a change in diameter of the lateral pipe.

* * * * *